(12) United States Patent
Chang et al.

(10) Patent No.: US 9,194,777 B2
(45) Date of Patent: Nov. 24, 2015

(54) FILTER TEST STRIP

(71) Applicant: Bioptik Technology, INC., Miaoli County (TW)

(72) Inventors: Ya-Yuan Chang, Miaoli County (TW); Chin-Shan Lai, Miaoli County (TW); Chin-Chang Yang, Miaoli County (TW); Kun-Lieh Wu, Miaoli County (TW)

(73) Assignee: BIOPTIK TECHNOLOGY, INC., Miaoli County (TW)

( * ) Notice: Subject to any disclaimer, the term of this patent is extended or adjusted under 35 U.S.C. 154(b) by 195 days.

(21) Appl. No.: 13/770,704

(22) Filed: Feb. 19, 2013

(65) Prior Publication Data
US 2013/0280800 A1 Oct. 24, 2013

(30) Foreign Application Priority Data
Apr. 19, 2012 (TW) .............................. 101207263 U

(51) Int. Cl.
| | | |
|---|---|---|
| G01N 21/75 | (2006.01) | |
| G01N 1/34 | (2006.01) | |
| G01N 33/52 | (2006.01) | |
| G01N 33/558 | (2006.01) | |
| G01N 1/40 | (2006.01) | |
| G01N 27/42 | (2006.01) | |
| G01N 15/00 | (2006.01) | |

(52) U.S. Cl.
CPC ................ *G01N 1/34* (2013.01); *G01N 33/525* (2013.01); *G01N 33/558* (2013.01); *B01L 2300/0681* (2013.01); *B01L 2300/0816* (2013.01); *B01L 2300/0825* (2013.01); *B01L 2300/0887* (2013.01); *G01N 27/42* (2013.01); *G01N 27/423* (2013.01); *G01N 2001/4088* (2013.01); *G01N 2015/0065* (2013.01); *G01N 2458/00* (2013.01)

(58) Field of Classification Search
CPC ................ B01L 2300/0681; B01L 2300/0816; B01L 2300/0825; B01L 2300/0887; G01N 2001/4088; G01N 2015/0065; G01N 21/78; G01N 2458/00; G01N 27/42; G01N 27/423
USPC ......... 422/52, 73, 82.01, 82.05, 82.08, 82.09, 422/82.11, 99, 102, 400, 401, 420, 421, 422/422, 423, 424, 425, 426, 427, 428, 429, 422/68.1, 82.06, 407, 501, 502, 503, 504; 436/164, 177, 43, 63
See application file for complete search history.

(56) References Cited

U.S. PATENT DOCUMENTS

| | | | | |
|---|---|---|---|---|
| 5,762,770 | A * | 6/1998 | Pritchard et al. | 204/403.14 |
| 6,942,769 | B2 * | 9/2005 | Cheng et al. | 204/400 |
| 8,012,428 | B2 * | 9/2011 | Dilleen et al. | 422/402 |
| 2010/0311149 | A1 * | 12/2010 | Bae et al. | 435/287.1 |

* cited by examiner

*Primary Examiner* — Dennis M White
(74) *Attorney, Agent, or Firm* — Muncy, Geissler, Olds & Lowe, P.C.

(57) ABSTRACT

A filter test strip to filter and test a specimen in liquid includes a test element and a specimen filter assembly which is located on the test element and includes a filter cotton holding layer, a filter cotton layer and a cotton bonding layer. The filter cotton holding layer has a filter channel to allow the specimen in liquid to pass through. The filter cotton layer fills the filter channel. A gap is formed between the filter cotton holding layer and filter cotton layer. The cotton bonding layer is located below the filter cotton holding layer and bonded to the test element via an adhesive which masks the gap. Hence the specimen in liquid can be prevented from seeping out through the gap with passing through the filter cotton layer. Therefore, the specimen in liquid can fully be filtered by the filter cotton layer to enhance test accuracy.

9 Claims, 7 Drawing Sheets bonding layer 33. In the drawing each of the aforesaid layers is

FILTER TEST STRIP

FIELD OF THE INVENTION

The present invention relates to a filter test strip and particularly to a filter structure for a filter test strip.

BACKGROUND OF THE INVENTION

Please refer to FIG. 1, a conventional filter test strip includes a filter cotton holding layer 1, a cotton bonding layer 2 and a test element 7. The filter cotton holding layer 1 and cotton bonding layer 2 are bonded by an adhesive 3 between them. The filter cotton holding layer 1 has a filter cotton 4 to filter blood 5 and remove blood cells to separate the blood cells and plasma, and allow only the plasma to pass through filter cotton to be captured. The plasma enters the test element 7 to be tested to get physiological data such as cholesterol, uric acid and the like.

In the aforesaid conventional structure, the filter cotton 4 is made of porous material to filter the blood cells of the blood 5 and separate the blood cells and plasma. However, the porous material tends to form uneven surfaces and gaps at the borders. When the filter cotton 4 is held in the filter cotton holding layer 1 gaps 6 are inevitably formed between the filter cotton 4 and filter cotton holding layer 1 that easily let the and blood cells to percolate through. Moreover, because the adhesive 3, the filter cotton 4 and cotton bonding layer 2 cannot form a tight bonding among them, some of the blood cells in the blood 5 tend to pass through the filter cotton 4 through the gaps 6 and between the filter cotton 4 and cotton bonding layer 2 to blend with the filtered blood 5 containing only the plasma. In other words, in the conventional structure the filter cotton 4 cannot fully filter out the blood cells in the blood 5. It contains residual blood cells during the test that affect test accuracy, thus cannot fully meet use requirements.

SUMMARY OF THE INVENTION

Therefore the primary object of the present invention is to provide a filter structure that can fully filter a specimen in liquid to meet use requirements.

To achieve the foregoing object, the present invention provides a filter test strip to filter and test a specimen in liquid. It includes a test element and a specimen filter assembly. The specimen filter assembly is located on the test element and includes at least one filter cotton holding layer, at least one filter cotton layer and at least one cotton bonding layer. The filter cotton holding layer has a filter channel to allow the specimen in liquid to pass through. The filter cotton layer fills the corresponding filter channel. A gap is formed between the filter cotton holding layer and filter cotton layer. The cotton bonding layer is located below the filter cotton holding layer and bonded to the test element via an adhesive which fully covers the circumference of the filter channel and masks the gap between the filter cotton holding layer and filter cotton layer.

By means of the structure set forth above, with the adhesive fully covering the circumference of the filter channel to mask the gap between the filter cotton holding layer and filter cotton layer, the specimen in liquid can fully pass through the filter cotton layer, hence test accuracy can be improved to meet use requirements.

The foregoing, as well as additional objects, features and advantages of the invention will be more readily apparent from the following detailed description, which proceeds with reference to the accompanying drawings.

DETAILED DESCRIPTION OF THE PREFERRED EMBODIMENTS

Figure 1:
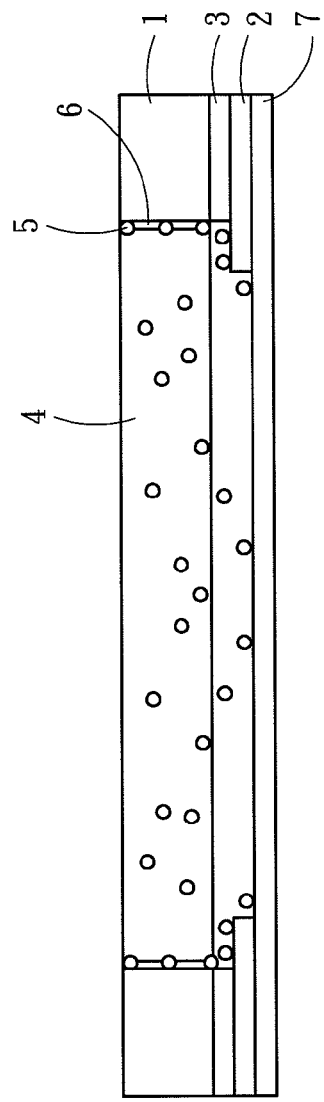
FIG. 1 is a schematic view of a conventional filter test strip.
Figure 2:
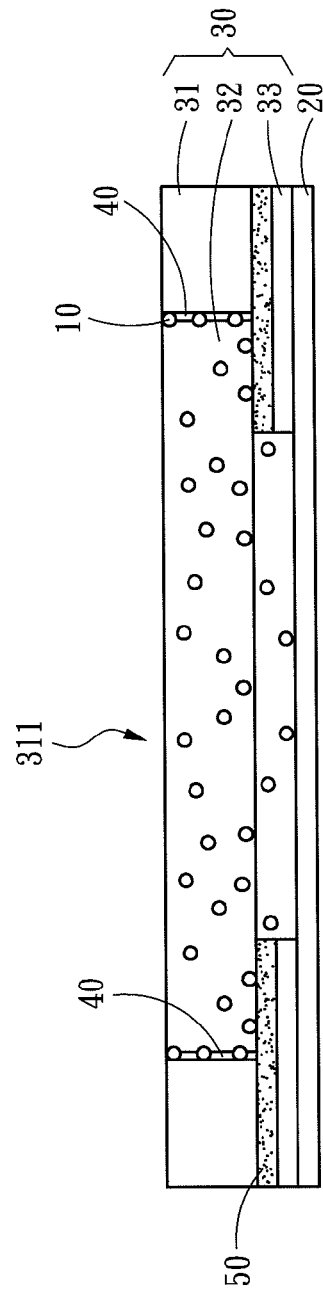
FIG. 2 is a schematic view of the filter structure of the filter test strip of the invention.

Please refer to FIG. 2, the present invention aims to provide a filter test strip to filter and test a specimen in liquid 10. It includes a test element 20 and a specimen filter assembly 30. The specimen filter assembly 30 is located on the test element 20, and includes at least one filter cotton holding layer 31, at least one filter cotton layer 32 and at least one cotton bonding layer 33. In the drawing each of the aforesaid layers is depicted by one set as an example for discussion. The filter cotton holding layer 31 has a filter channel 311 to allow the specimen in liquid 10 to pass through. The filter cotton layer 32 fills the corresponding filter channel 311. A gap 40 is formed between the filter cotton holding layer 31 and filter cotton layer 32. The gap 40 shown in the drawing is enlarged to facilitate discussion, and not the actual size. The cotton bonding layer 33 is located below the filter cotton holding layer 31 and bonded to the test element 20 via an adhesive 50. The adhesive 50 on the cotton bonding layer 33 fully covers the circumference of the filter channel 311 and masks the gap 40 between the filter cotton holding layer 31 and filter cotton layer 32.

Figure 3:
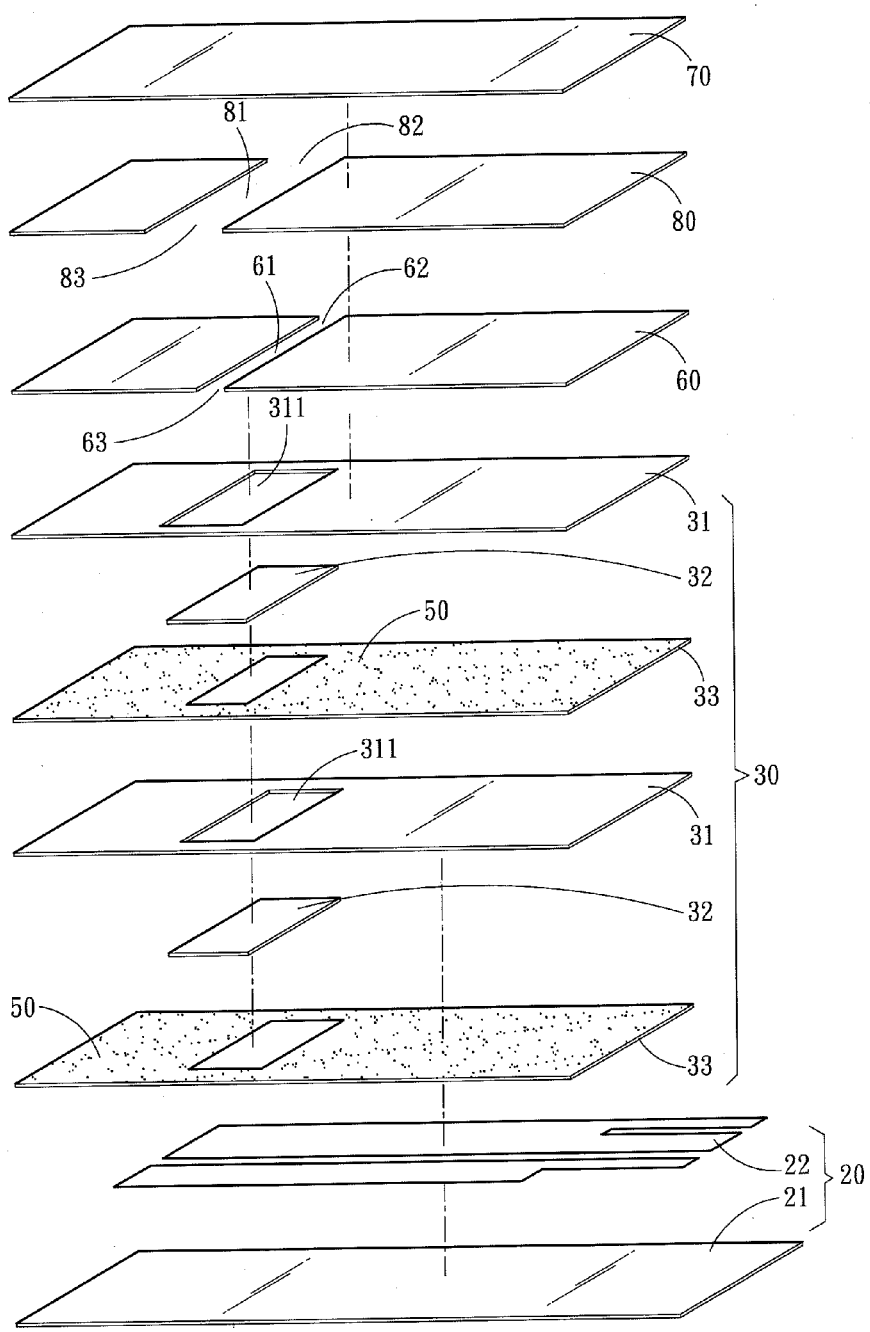
FIG. 3 is an exploded view of a first embodiment of the invention.
Figure 4A:
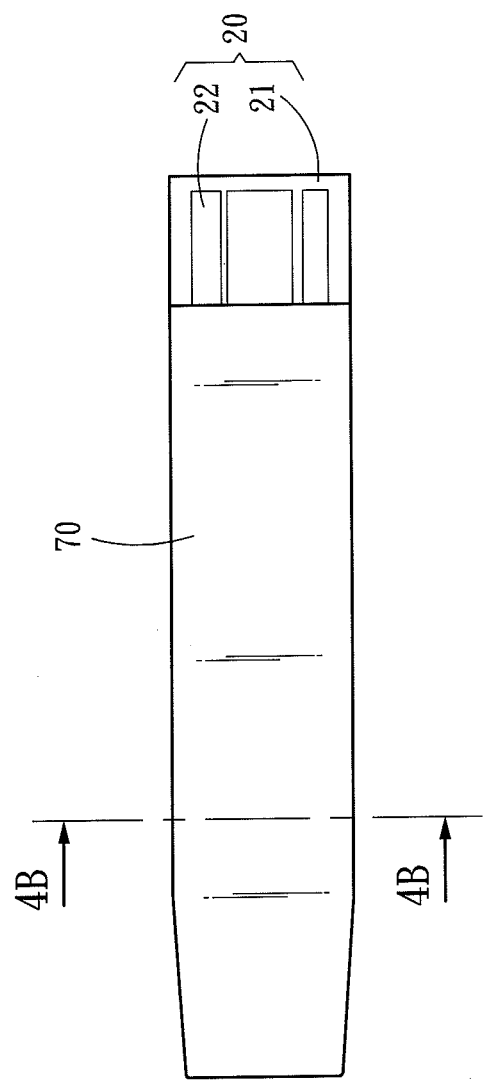
FIG. 4A is a front view of the first embodiment of the invention.
Figure 4B:
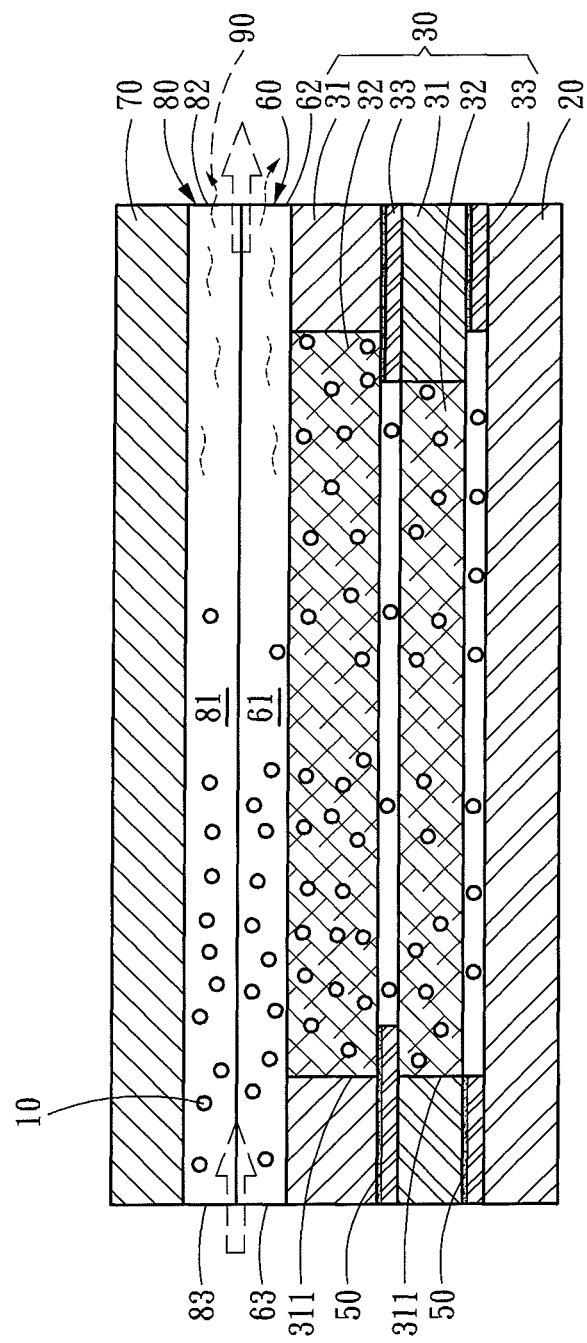
FIG. 4B is a cross section taken on line 4B-4B in FIG. 4A.

Please refer to FIGS. 3, 4A and 4B for a first embodiment of the invention. In this embodiment, the filter cotton holding layer 31, filter cotton layer 32 and cotton bonding layer 33 have respectively two sets as an example for discussion. It also includes a cotton press layer 60 and an upper lid 70 that sequentially cover the specimen filter assembly 30 and mask the filter channel 311 to protect the specimen filter assembly 30. The cotton press layer 60 has a passage 61 to receive the specimen in liquid 10 from outside and communicate with the filter channel 311. The passage 61 transversely runs through the cotton press layer 60 to form an air outlet 62 for discharging air 90 and a specimen inlet 63 for receiving the specimen in liquid 10. In practice, the air outlet 62 and specimen inlet 63 can be switched in positions as desired to suit users' hand using habits.

The invention, according to another embodiment, can also include a passage layer 80 located between the cotton press layer 60 and upper lid 70. The passage layer 80 has an ancillary passage 81 corresponding to the passage 61 and formed at an area greater than that of the passage 61. The ancillary passage 81 also transversely runs through the passage layer 80 to form an ancillary air outlet 82 for discharging the air 90 and an ancillary specimen inlet 83 for receiving the specimen in liquid 10. The ancillary specimen inlet 83 can increase space for the specimen in liquid 10 to enter, and the ancillary air outlet 82 can improve air discharge effect so that entry of the specimen in liquid 10 is easier to enhance test sensitivity. The test element 20 can include a substrate 21 and an electrode 22 formed on the substrate 21 to contact the filter channel 311.

Figure 5:
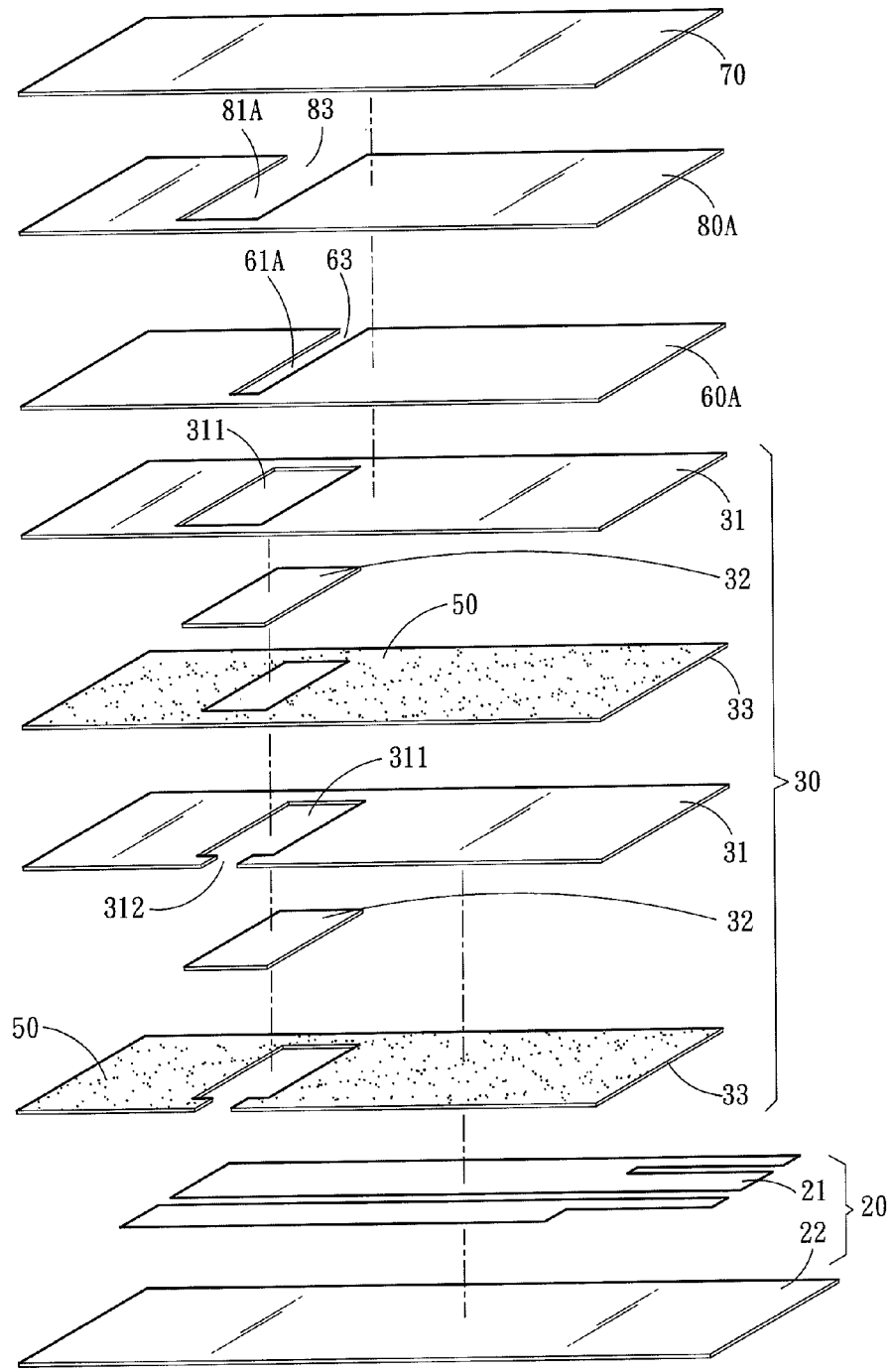
FIG. 5 is an exploded view of a second embodiment of the invention.
Figure 6A:
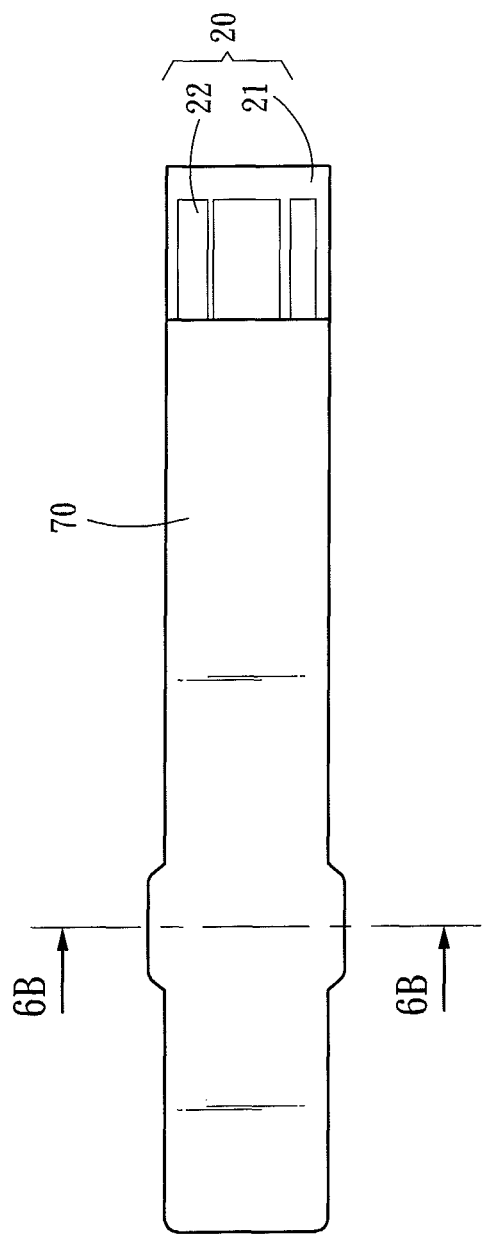
FIG. 6A is a front view of the second embodiment of the invention.
Figure 6B:
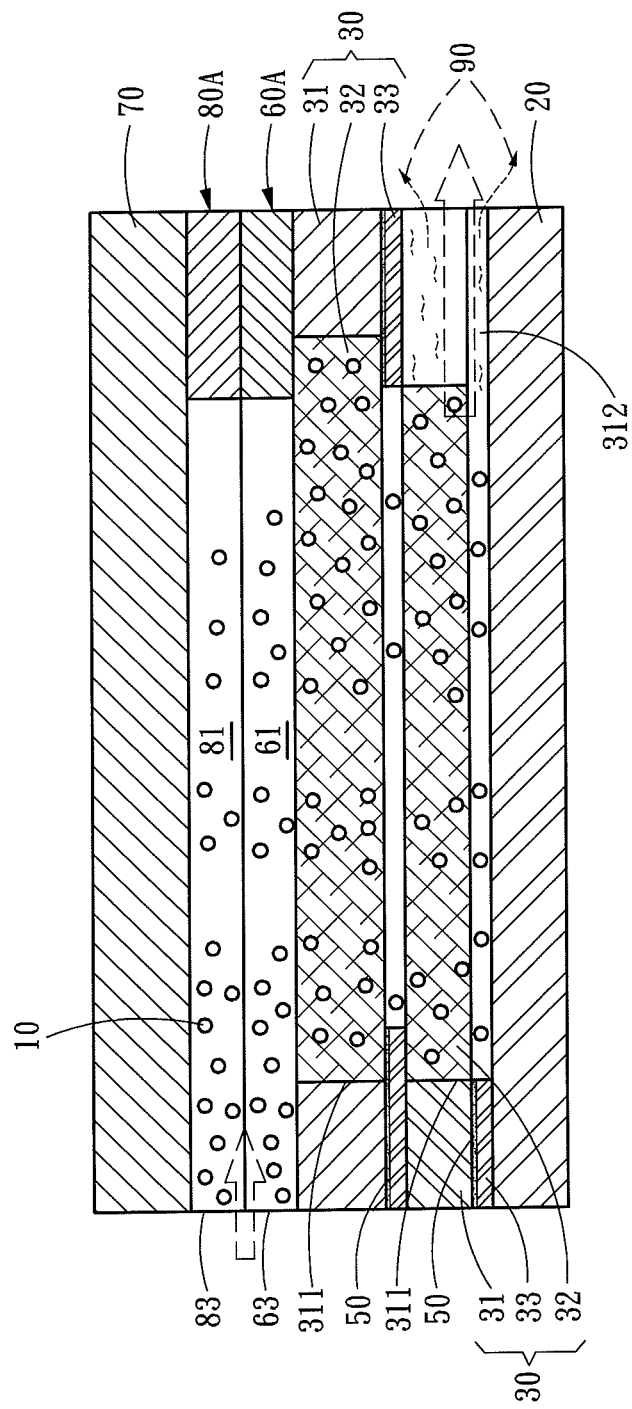
FIG. 6B is a cross section taken on line 6B-6B in FIG. 6A.

Please refer to FIGS. 5, 6A and 6B for a second embodiment of the invention. It differs from the first embodiment by the cotton press layer 60A having a passage 61A to receive the specimen in liquid 10 from outside. The passage 61A communicates with the filter channel 311 and has a specimen inlet 63 to receive the specimen in liquid 10. The filter cotton holding layer 31 includes an output channel 312 communicating with outside and the filter channel 311. The output channel 312 can discharge the air 90. Similarly, a passage layer 80A also is provided between the cotton press layer 60A and upper lid 70. The passage layer 80A also has an ancillary passage 81A corresponding to the passage 61A and formed at an area greater than that of the passage 61A. The ancillary passage 81A also has an ancillary specimen inlet 83 to receive the specimen in liquid 10. Through the ancillary specimen inlet 83 and output channel 312, a structure with liquid entry at the upper side and air discharge at the lower side is formed to make entry of the specimen in liquid 10 easier.

As a conclusion, in the invention, with the adhesive extended to fully cover the circumference of the filter channel and mask the gap between the filter cotton holding layer and filter cotton layer, the specimen in liquid can be prevented from seeping out through gap with passing through the filter cotton layer, thereby the specimen in liquid can fully be filtered by the filter cotton layer to improve test accuracy and meet use requirements.

What is claimed is:

1. A filter test strip to filter and test a specimen in liquid, comprising:
   a test element; and
   a specimen filter assembly which is located on the test element and includes at least one filter cotton holding layer, at least one filter cotton layer and at least one cotton bonding layer; the filter cotton holding layer including a plurality of inner side walls to define a filter channel to allow the specimen in liquid to pass through, the filter cotton layer filling within the corresponding filter channel, the plurality of inner side walls and the filter cotton layer being spaced by a gap, the cotton bonding layer being located below the filter cotton holding layer, the filter cotton holding layer including a surface which faces the cotton bonding layer and bonds to the cotton bonding layer via an adhesive to make the whole surface of the filter cotton holding contact the contact bonding layer, the adhesive fully covering a circumference of the filter channel and masking the gap between the plurality of inner side walls and the filter cotton layer.

2. The filter test strip of claim 1 further including a cotton press layer and an upper lid that sequentially cover the specimen filter assembly and mask the filter channel, the cotton press layer including a passage to receive the specimen in liquid from outside and communicate with the filter channel.

3. The filter test strip of claim 2, wherein the passage transversely runs through the cotton press layer to form an air outlet and a specimen inlet.

4. The filter test strip of claim 3 further including a passage layer located between the cotton press layer and the upper lid, the passage layer including an ancillary passage formed at an area greater than that of the passage and corresponding to the passage.

5. The filter test strip of claim 4, wherein the ancillary passage transversely runs through the passage layer to form an ancillary air outlet and an ancillary specimen inlet.

6. The filter test strip of claim 1, wherein the test element includes a substrate and an electrode formed on the substrate to contact the filter channel.

7. The filter test strip of claim 2, wherein the passage includes a specimen inlet, the filter cotton holding layer including an output channel communicating with the outside and the filter channel.

8. The filter test strip of claim 7 further including a passage layer located between the cotton press layer and the upper lid, the passage layer including an ancillary passage formed at an area greater than that of the passage and corresponding to the passage.

9. The filter test strip of claim 8, wherein the ancillary passage including an ancillary specimen inlet.

\* \* \* \* \*